US008397475B2

(12) United States Patent
Boekstegers et al.

(10) Patent No.: US 8,397,475 B2
(45) Date of Patent: Mar. 19, 2013

(54) PACKAGING MACHINE WITH GAS CONCENTRATION MEASURING DEVICE

(75) Inventors: Hans-Joachim Boekstegers, Starnberg (DE); Tobias Richter, Memmingen (DE)

(73) Assignee: Multivac Sepp Haggenmueller GmbH & Co. KG (DE)

( * ) Notice: Subject to any disclaimer, the term of this patent is extended or adjusted under 35 U.S.C. 154(b) by 275 days.

(21) Appl. No.: 12/786,748

(22) Filed: May 25, 2010

(65) Prior Publication Data

US 2010/0293899 A1 Nov. 25, 2010

(30) Foreign Application Priority Data

May 25, 2009 (DE) .......................... 10 2009 022 545

(51) Int. Cl.
*B65B 31/02* (2006.01)
*B65B 57/00* (2006.01)
(52) U.S. Cl. .............. 53/507; 53/86; 53/510; 250/222.1
(58) Field of Classification Search .................... 53/510, 53/511, 79, 86, 507, 508, 559, 561; 73/52; 250/222.1; 356/239.6, 240.1, 439
See application file for complete search history.

(56) References Cited

U.S. PATENT DOCUMENTS

| 5,071,667 A * | 12/1991 | Grune et al. .............. 53/510 |
| 5,407,829 A | 4/1995 | Wolfbeis et al. |
| 5,458,896 A * | 10/1995 | Porter .................. 436/172 |
| 5,511,547 A | 4/1996 | Markle et al. |
| 5,822,951 A | 10/1998 | Rosik |
| 5,826,632 A * | 10/1998 | Micke et al. ............. 141/9 |
| 6,185,913 B1 * | 2/2001 | Cappi et al. ............ 53/511 |
| 6,267,158 B1 * | 7/2001 | Saga .................... 141/94 |
| 6,305,148 B1 * | 10/2001 | Bowden et al. ........... 53/510 |
| 7,569,395 B2 | 8/2009 | Havens et al. |
| 7,950,207 B2 * | 5/2011 | Maisel .................. 53/510 |
| 2004/0086749 A1 * | 5/2004 | Kennedy et al. ........... 428/690 |

(Continued)

FOREIGN PATENT DOCUMENTS

DE 69318564 T2 11/1998
DE 102007013698 A1 6/2008

(Continued)

OTHER PUBLICATIONS

German Search Report Dated Feb. 26, 2010, Applicant Multivac Sepp Haggenmueller GmbH & Co., KG, Application No. 10 2009 022 545.5-27, 4 pages.

(Continued)

*Primary Examiner* — Stephen F Gerrity
(74) *Attorney, Agent, or Firm* — Brooks Kushman P.C.

(57) ABSTRACT

A packaging machine for producing closed packages includes a chamber that can be sealed in an airtight manner around one or a plurality of packages, a gas flushing unit for flushing with a gas the at least one package contained in the chamber, at least one gas line leading into the chamber or out of the chamber as well as a measuring device for determining a concentration of the gas. The measuring device comprises a measuring head for reading, through the use of electromagnetic radiation, an indicator for the concentration of the gas. The indicator is arranged in an interior of the chamber, in an interior of a package and/or in an interior the at least one gas line.

23 Claims, 5 Drawing Sheets

U.S. PATENT DOCUMENTS

| | | | |
|---|---|---|---|
| 2007/0151209 A1* | 7/2007 | Trpkovski | 53/79 |
| 2007/0212789 A1 | 9/2007 | Havens et al. | |
| 2008/0152767 A1 | 6/2008 | Maisel | |

FOREIGN PATENT DOCUMENTS

| | | |
|---|---|---|
| DE | 69516272 T2 | 8/2008 |
| EP | 0 627 363 A1 | 12/1994 |
| WO | 9324820 A1 | 12/1993 |
| WO | 96/02438 A1 | 2/1996 |
| WO | 2006101651 A1 | 9/2006 |
| WO | 2008074917 A1 | 6/2008 |

OTHER PUBLICATIONS

European Search Report Dated Sep. 1, 2010, Application No. 1004870.1-2308, Applicant Multival Sepp Haggenmueller GmbH & Co. KG, 6 pages.

* cited by examiner

PACKAGING MACHINE WITH GAS CONCENTRATION MEASURING DEVICE

CROSS-REFERENCE TO RELATED APPLICATIONS

This application claims foreign priority benefits under 35 U.S.C. §119(a)-(d) to German patent application number DE 10 2009 022 545.5, filed May 25, 2009, which is incorporated by reference in its entirety.

TECHNICAL FIELD

The present invention relates to a packaging machine for producing closed packages.

BACKGROUND

Such packaging machines are not only known in practice, but they are also known e.g. from DE 10 2007 013 698 A1. They are based on the finding that packed products can have a particularly long shelf life when a specific concentration of a specific gas (or of a plurality of gases), which deviates from the ambient air, exists in the package. It follows that, before the package filled with the product in question is closed in a gastight manner, this gas or gas mixture is introduced in the package in the ideal concentration, after the ambient air previously contained in the package has been, or is being evacuated from the package.

For obtaining the longest possible shelf life of the products, it is necessary that the gas or gas mixture concentration neither falls below nor exceeds the ideal concentration range of the gas or gas mixture. It follows that the gas mixture introduced and contained in the packages and the leak tightness of the chamber will be have to be measured regularly. For this purpose, conventional packaging machines were equipped with a gas concentration sensor which, via a measurement input, took a gas sample from the packaging machine chamber used for gas flushing, and evaluated this sample. The measurement value represented the reference value for all the packages contained in the chamber.

This conventional measurement principle has various drawbacks. On the one hand, there is a delay in the measurement, since the gas sample must first be transferred to the gas sensor via the measurement gas line. On the other hand, the measurement values will be flawed with inaccuracies, when the measurement line of the gas sensor has not been fully flushed with the filling gas of the new cycle prior to carrying out a new measurement. Moreover, there is the risk that, together with the gas sample, residues of liquids or dirt arrive at the gas sensor, which may not only corrupt the measurement values but also damage the gas sensor permanently.

SUMMARY

It is an object of the present disclosure to improve, with the aid of means that may have the simplest possible structural design, the known packaging machine in such a way that a fast, reliable measurement of the gas concentration will be possible.

According to the present disclosure, an indicator for the concentration of the gas is provided, the indicator being arranged in the interior of the chamber, in the interior of a package and/or in the interior of a gas line. The measuring device for determining the gas concentration is, in turn, provided with a measuring head that is able to read the indicator by means of electromagnetic radiation.

An advantage according to an embodiment of the present disclosure resides in the fact that it is no longer necessary to take gas samples for measuring the concentration of the gas or of a gas mixture. Instead, only the indicator is arranged in the interior of the chamber, in the interior of a package and/or in the interior of a gas line, and, consequently, at a location where it can interact with the gas or gas mixture. The measuring head itself, however, need no longer come into direct contact with the gas volume to be measured. In this way, the measurement can be carried out extremely fast, since the indicator is read with electromagnetic radiation, i.e. at light velocity. The time-consuming step of bringing a gas sample to the gas sensor can be dispensed with. In addition, the measurement results will be much more reliable, since they cannot be corrupted by residual gases in the measurement gas input of the gas sensor originating e.g. from a preceding work cycle of the packaging machine.

In principle, radiation of any region of the electromagnetic spectrum may be used for reading the indicator, as long as the indicator is able to interact with this radiation. The electromagnetic radiation may e.g. be UV light, infrared light, terahertz radiation, low-frequency or high-frequency radio waves. Preferably, the indicator will, however, be read in the visible or "optical" spectral region, since a large number of small-sized measuring heads is available in this region.

According to one embodiment, the measuring head is arranged in the wall of the chamber or of the gas line, without being, however, in direct contact with the interior of the chamber or of the gas line. This mode of arrangement allows a direct, reliable measurement of the concentration of the gas or gas mixture, without the risk of contaminating or damaging the measuring head.

It is imaginable that the measuring device only reads the indicator. It will, however, be of advantage when the measuring device also optically activates the indicator, e.g. by transmitting light to the indicator (or by applying electromagnetic radiation outside the visible region to the indicator). Due to this activation of the indicator, the sensitivity of the measurement can be increased significantly.

It will be expedient, when the measuring head is configured for measuring the reflectivity, the transmissivity and/or the fluorescence of the indicator in a specific spectral region or at a specific wavelength. For this purpose, suitable filters may be provided, which suppress noise in the measurement and which thus increase the measurement sensitivity still further.

It would be imaginable to provide the packaging machine with a unit for varying and adjusting the spectral region in which, or the wavelength at which the measuring head reads the indicator. The variation of the spectral region or of the wavelength could take place automatically so as to optimize e.g. the accuracy of the measurement. The spectral region or the wavelength may also be varied and adjusted—automatically or manually—for the purpose of measuring concentrations of different gases or gas mixtures, if said measurement should be executable in a particularly effective manner in different spectral regions or at different wavelengths.

In view of the spatial separation of the indicator and the measuring head, the packaging machine can be provided with a device for cleaning the indicator. It can thus be guaranteed that the measurements will not be corrupted by particles or residues of liquid adhering to the indicator. Cleaning of the indicator can also be executed in a so-called "clean-in-place" process, if desired between two package closing cycles.

According to one embodiment of the present disclosure, it is possible that the packaging machine comprises means for providing an indicator in a package. The gas concentration in an individual package can be measured in this way, even when the package has been closed, and, if necessary, even for examining the packages when they are stored at a warehouse or immediately before they are sold on the market. For the purpose of quality control, the values measured for each individual package may be stored. Especially in the case of health-relevant products, such as products belonging to the field of medical technology or pharmaceutical products, this may be of advantage so as to be able to counteract future liability claims on the grounds of an allegedly incorrect flushing with gas or leakiness of the packages.

In this respect, it would e.g. be expedient, if the means for providing an indicator were configured for attaching an indicator to the side of a cover sheet which faces a container part of the package and which will be connected to said container part later on.

In the following, an advantageous embodiment of the present disclosure will be explained in more detail on the basis of a drawing, in which:

DETAILED DESCRIPTION

Figure 1:
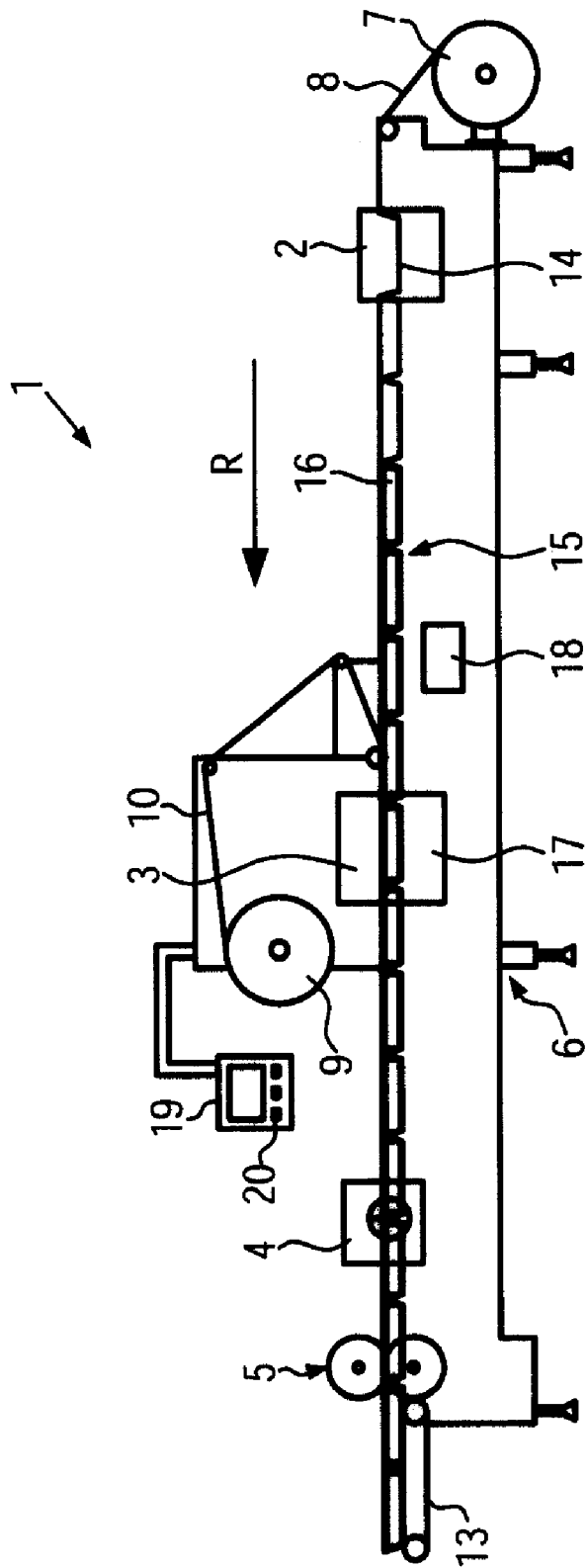
FIG. 1 shows a schematic side view of a packaging machine according to the present disclosure in the form of a deep drawing packaging machine.

Identical components are designated by identical reference numerals in all the figures.

FIG. 1 shows in a schematic view a packaging machine 1 according to the present disclosure in the form of a deep drawing packaging machine. This deep drawing packaging machine 1 comprises a forming station 2, a sealing station 3, a transverse cutting device 4 and a longitudinal cutting device 5, which are arranged in this order in the working direction R at a machine frame 6. On the input side, a supply roll 7 is provided on the machine frame 6, from which a first web material 8 is unwound. In the area of the sealing station 3, a material storage unit 9 is provided, from which a second web material 10 used as a cover sheet is unwound. On the output side, a discharge device 13 in the form of a conveyor belt is provided at the packaging machine, with which finished, singulated packages are transported away. Furthermore, the packaging machine 1 comprises a feed device which is not shown, said feed device gripping the first web material 8 and transporting it cyclically in a main work cycle in the working direction R. The feed device can be realized, for example, by laterally arranged transport chains.

In the embodiment shown, the forming station 2 is realized as a deep drawing station in which containers 14 are formed in the first web material 8 by deep drawing. The forming station 2 can be configured in such a way that in the direction perpendicular to the working direction R several containers are formed side by side. In the working direction R behind the forming station 2, a filling area 15 is provided, in which the containers 14 formed in the first web material 8 are filled with the product 16.

The sealing station 3 is provided with a closable chamber 17 in which the atmosphere in the container 14 can, prior to sealing, be substituted by a substitute gas or by a substitute gas mixture, e.g. by means of gas flushing.

The transverse cutting device 4 is configured as a punch separating the first web material 8 and the second web material 10 in a direction transversely to the working direction R between neighbouring containers 14. In so doing, the transverse cutting device 4 works such that the first web material 8 is not cut across the whole width of the web, but remains uncut in at least a boundary area. This allows controlled further transport by the feed device.

In the embodiment shown, the longitudinal cutting device 5 is configured as a blade arrangement by means of which the first web material 8 and the second web material 10 are cut between neighbouring containers 14 and at the lateral edge of the first web material 8, so that, downstream of the longitudinal cutting device 5, singulated packages are obtained.

The packaging machine 1 is additionally provided with a control unit 18. It is used for controlling and monitoring the processes taking place in the packaging machine 1. A display device 19 with operating controls 20 serves to visualize the sequences of process steps in the packaging machine 1 for an operator and to influence them by the operator.

The general mode of operation of the packaging machine 1 will be described briefly in the following.

The first web material 8 is unwound from the supply roll 7 and conveyed into the forming station 2 by the feed device. In the forming station 2, containers 14 are formed in the first web material 8 by deep drawing. In a main work cycle, the containers 14 are advanced, together with the portion of the first web material 8 surrounding them, to the filling area 15 where they are filled with the product 16.

Subsequently, the filled containers 14, together with the portion of the first web material 8 surrounding them, are advanced by the feed device into the sealing station 3 in said main work cycle. After having been sealed onto the first web material 8, the second web material 10 is advanced as a cover sheet with the feed motion of the first web material 8. In the course of this process, the second web material 10 is unwound from the material storage unit 9. By sealing the cover sheet 10 onto the containers 14, closed packages 21 are obtained.

Figure 2:
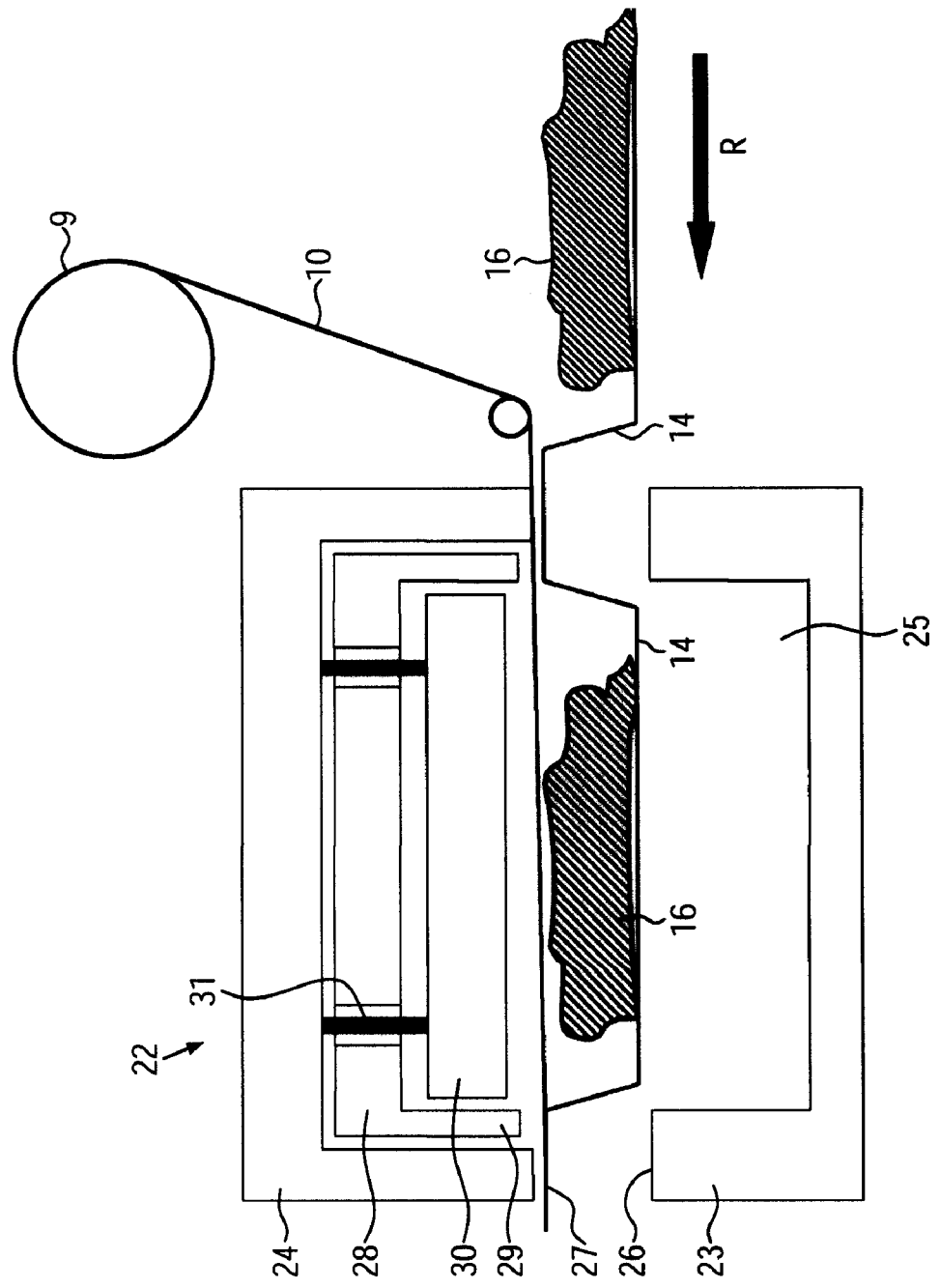
FIG. 2 shows a schematic vertical section through the sealing tool of the packaging machine shown in FIG. 1, at an open position.

FIG. 2 shows in a schematic representation a vertical section through a sealing tool 22 of the sealing station 3. The sealing tool 22 comprises a sealing tool bottom 23 and a sealing tool top 24. The sealing tool bottom 23 has provided therein a hollow or cavity 25. The cavity 25 can have arranged therein a container 14 to be closed, whereas the edge 26 of the sealing tool bottom 23 carries the edge 27 of the container 14.

In the interior of the sealing tool top 24 there is a sealing plate 28 with downwardly projecting sealing edges 29. A product protection plate 30 is provided within the sealing plate 28. The product protection plate 30 is cooler than the sealing plate 28 and prevents excessive heating of the product 16 in the container 14 during the sealing process. For this purpose, cooling water lines 31 for cooling the product protection plate 30 can be provided.

Figure 3:
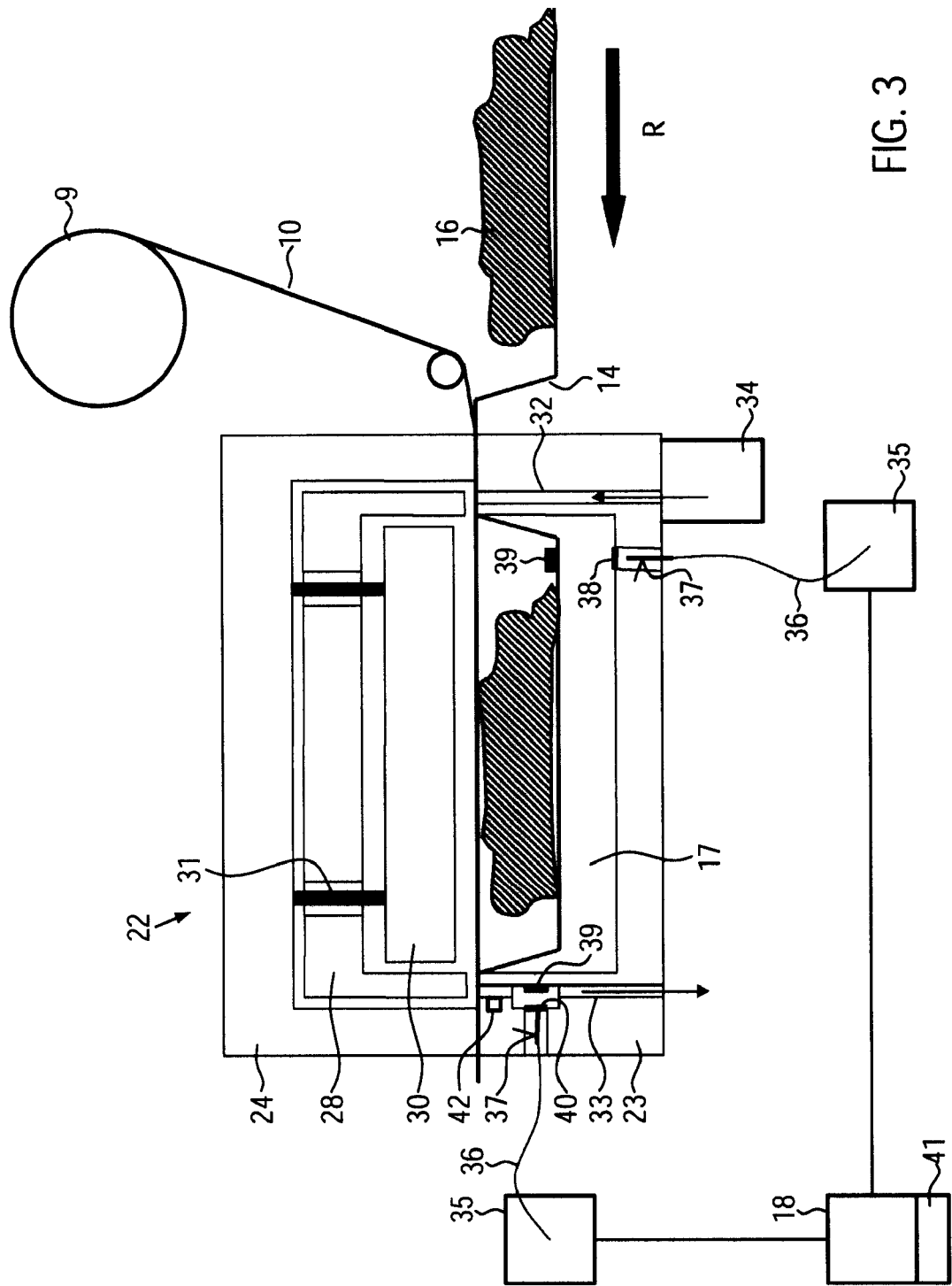
FIG. 3 shows the sealing tool depicted in FIG. 2, at a closed position.

FIG. 3 shows the sealing tool 22 according to FIG. 2 in a condition in which the sealing tool bottom 23 and the sealing tool top 24 have been closed around a container 14 so as to form a closed chamber 17. In this condition, the edge 27 of the container 14 and the overlying cover sheet 10 are clamped in an airtight manner between the lower edge of the sealing tool top 24 and the edge 26 of the sealing tool bottom 23. The chamber 17 is sealed in an airtight manner all around the container 14.

In this condition, i.e. before the cover sheet 10 is sealed onto the container 14, the container 14 is flushed with gas. To this end, a plurality of gas lines is provided in the sealing tool bottom 23, viz. a gas supply line 32 and a gas discharge line 33. The gas lines 32, 33 belong to an evacuating and gas flushing unit 34, which is shown schematically in FIG. 3. The evacuating and gas flushing unit 34 is configured to introduce a gas or a gas mixture (e.g. oxygen or $CO_2$) extending the shelf life of the product 16 via the gas supply line 32 into the chamber 17 as well as to evacuate the chamber 17 by means of the gas discharge line 33. Evacuation and gas flushing can take place successively or simultaneously. In order to guarantee that the gas supply line 32 and the gas discharge line 33 communicate with the interior of the container 14, means (not shown), such as movable pins, are provided which lift the cover sheet 10 from the openings of the gas lines 32, 33 during evacuation and/or gas flushing.

The packaging machine 1 comprises one or a plurality of measuring devices 35 provided on the sealing tool 22 and used for determining a concentration of the gas or gas mixture introduced in the chamber 17. In the embodiment according to FIG. 3, two measuring devices 35 are provided. Each of these measuring devices 35 is connected to a measuring head 37 via a light guide 36. Each of the two measuring heads 37 is placed in the wall of the sealing tool bottom 23. One of the measuring heads 37 is separated from the interior of the chamber 17 by a window 38. The window 38 protects the measuring head 37, but it is transparent to electromagnetic radiation emitted from and received by the measuring head 37. The window 38 is strong enough for not being damaged during evacuation of the chamber 17. Directly in the line of sight of the measuring head 37, an indicator 39 is located in the interior of the chamber 17 or, in the present case, even in the interior of the container 14. The indicator 39 interacts with the electromagnetic radiation emitted from and received by the measuring head 37; this radiation may especially be radiation in the visible spectral region or in a spectral region proximate to the visible spectral region, e.g. with wavelengths between 300 nm and 2 μm. The indicator 39 is so conceived that its characteristics will change, when it interacts with the electromagnetic radiation, in dependence upon the concentration of the gas or gas mixture to be measured.

The other measuring head 37 is separated from the gas discharge line 33 by a window 40. Also this window 40 is transparent to the electromagnetic radiation emitted by or received from the measuring head 37, and it is also stable enough for not being damaged by gas flushing and/or evacuation of the chamber 17. An indicator 39 is arranged in the line of sight of the measuring head 37 on the inner wall of the gas discharge line 33 located opposite the window 40.

The operation of the sealing tool 22 of the packaging machine 1 takes place as described hereinbelow. When the container 14, i.e. a not yet closed package 21, has been introduced in the sealing tool 22, the sealing tool bottom 23 and the sealing tool top 24 are moved towards one another until they unite, thus forming a chamber 17 around the package 14. The use of suitable means guarantees that the cover sheet 10 remains in spaced relationship with the container 14, at least in the area of the openings of the gas lines 32, 33 leading into the chamber 17. The chamber 17 and the interior of the container 14, respectively, can now first be evacuated via the gas discharge line 33. Subsequently, the gas flushing unit 34 sends a substitute gas or gas mixture to the container 14 via the gas supply line 32. The substitute gas may e.g. be $O_2$ or $CO_2$.

The measuring device 35 takes care that the indicator 39 will be read continuously or at regular intervals. To this end, a light pulse can be generated in the measuring device 35, e.g. by means of a laser. The light is conducted via the light guide 36 to the measuring head 37 from where it is transmitted via the window 38, 40 to the respective indicator 39. The indicator 39 absorbs the light and is thus activated for emitting fluorescent radiation. The fluorescent characteristics of the indicator 39 change in response to the concentration of the substitute gas. These fluorescent characteristics are ascertained by the measuring device 35 via the measuring head 37. The measuring device 35 is able to draw conclusions with respect to the gas concentration from the fluorescent characteristics. Indicators of this type are known for the optical region (but not for other spectral regions) e.g. from WO 2007/093774 A1.

The measuring devices 35 can be configured for spectroscopically reading the indicator 39. By means of a spectral analysis of the radiation received from the indicator 39, the measuring device 35 is e.g. able to determine a change in the spectrum at different wavelengths so as to draw conclusions with respect to the concentration of different gases therefrom.

The measuring devices 35 transmit their measurement data regularly to the control unit 18 of the packaging machine 1. The control unit 18 can be configured such that it will finish gas flushing as soon as a certain concentration of the substitute gas has been reached. The control unit 18 may also have provided thereon a memory 41 for the measurement values. This memory 41 allows storage of the measurement data obtained by means of the measuring devices 35. Especially when each package 14, 21 is provided with an indicator 39 of its own, it will be possible to store evidence that a specific atmosphere prevailed in the package 21 during production of said package 21. This may be relevant to product liability questions later on, especially when the products in question 16 are health-relevant products, such as pharmaceutical products or products belonging to the field of medical technology.

It is imaginable that the packaging machine 1 has provided thereon, e.g. in connection with the control unit 18, a unit for modifying and/or adjusting the spectral region in which or the wavelength at which the indicator 39 is read. For example, the unit may be an adjustable filter, such as an electronic or optical filter, that is provided as part of the respective measuring device 35. The spectral region in which or the wavelength at which the measurement takes place can thus be adjusted to a gas concentration measurement value which is optimal for the respective process conditions prevailing (pressure, temperature). They can also be varied so as to measure the concentration of different gases in different spectral regions or at different wavelengths, when the indicator 39 responds in these different spectral regions/at these different wavelengths to the respective gases in different ways.

The packaging machine 1 can additionally have provided therein a cleaning device 42 for an indicator, and the cleaning device 42 may be connected to, or otherwise in communication with, the control unit 18. In the embodiment according to FIG. 3, such a cleaning device 42 is located in the gas discharge line 33, a short distance above the indicator 39 when seen in the direction of flow. By means of the cleaning device 42 e.g. a gas or a liquid can be directed onto the indicator 39 so as to rinse the indicator 39 for removing liquid residues or dirt therefrom. This cleaning can take place in a so-called "clean-in-place" process (CIP).

Figure 4:
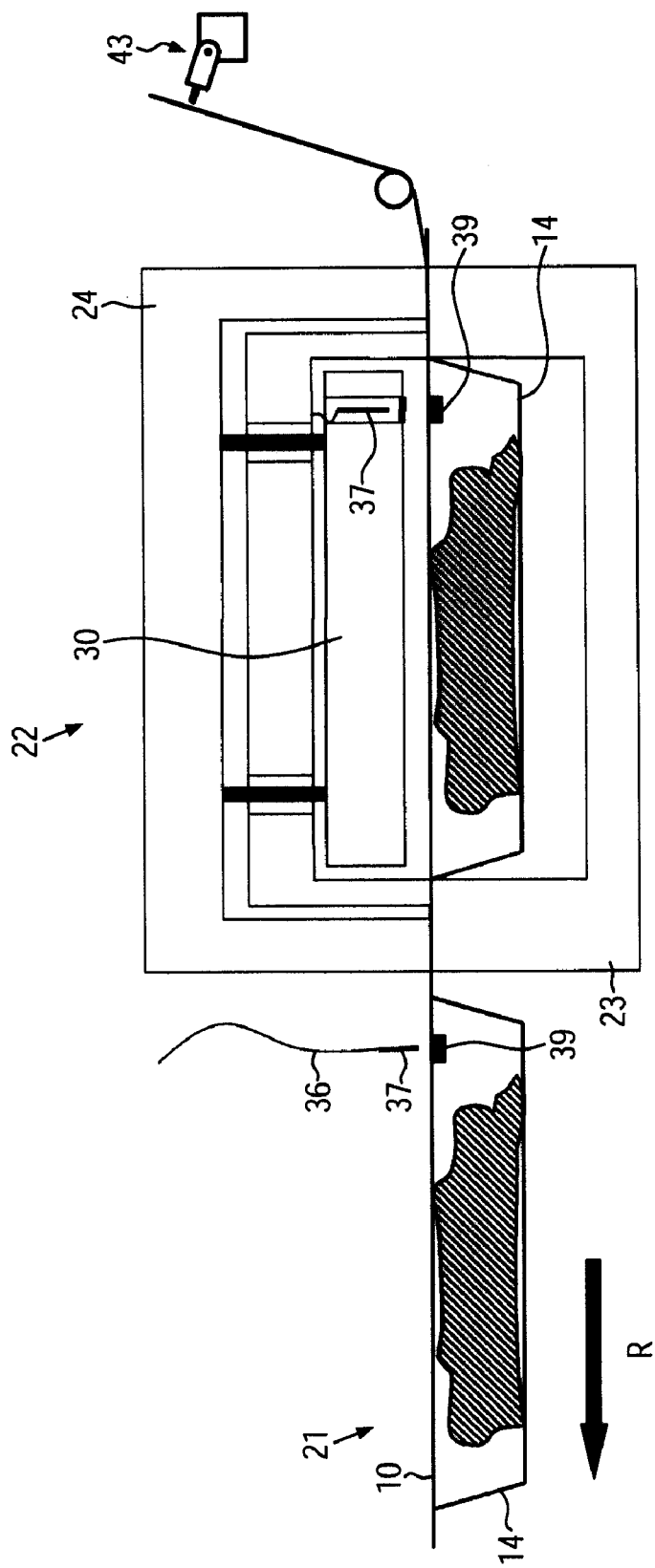
FIG. 4 shows a second embodiment of the sealing tool depicted in FIGS. 2 and 3.

FIG. 4 shows in a schematic form two additional embodiments of the packaging machine 1 according to the present disclosure. Both said embodiments have in common that the packaging machine 1 comprises means 43 for providing an indicator 39 in a package 21; with the aid of these means the indicator 39 may be attached to the side of the cover sheet 10 facing the container part 14 of the package 21, or to any other interior portion of the package 21. The means 43 may be any suitable device, such as a robot (e.g., movable robotic arm) or other positioning device, a labeling device that adheres the indicator 39 (which may be adhesive-backed, for example) to the package 21, or an indicator-forming device, such as a printing device (e.g., ink jet printer) that prints or otherwise forms the indicator 39 onto the cover sheet 10 or other portion of the package 21.

In a first variant of this embodiment, the measuring head 37 of the measuring device 35 is arranged outside the sealing tool 22, viz. behind the sealing tool 22 when seen in the direction of transport R. This measuring head 37 is arranged in such a way that it is oriented towards the indicator 39 provided in a package 21 positioned below said measuring head 37 and closed by means of the cover sheet 10. The gas concentration prevailing in the package interior when the package 21 has been closed can be measured precisely in this way.

In the other embodiment, which is shown on the right hand side, a measuring head 37 is arranged in the product protection plate 30 of the sealing tool 22. Also this measuring head 37 is arranged such that it is oriented towards an indicator 39 located therebelow in a package 21. At this location, the measuring head 37 is able to measure the gas concentration in the package 21 during the gas flushing as well as after the sealing process.

Figure 5B:
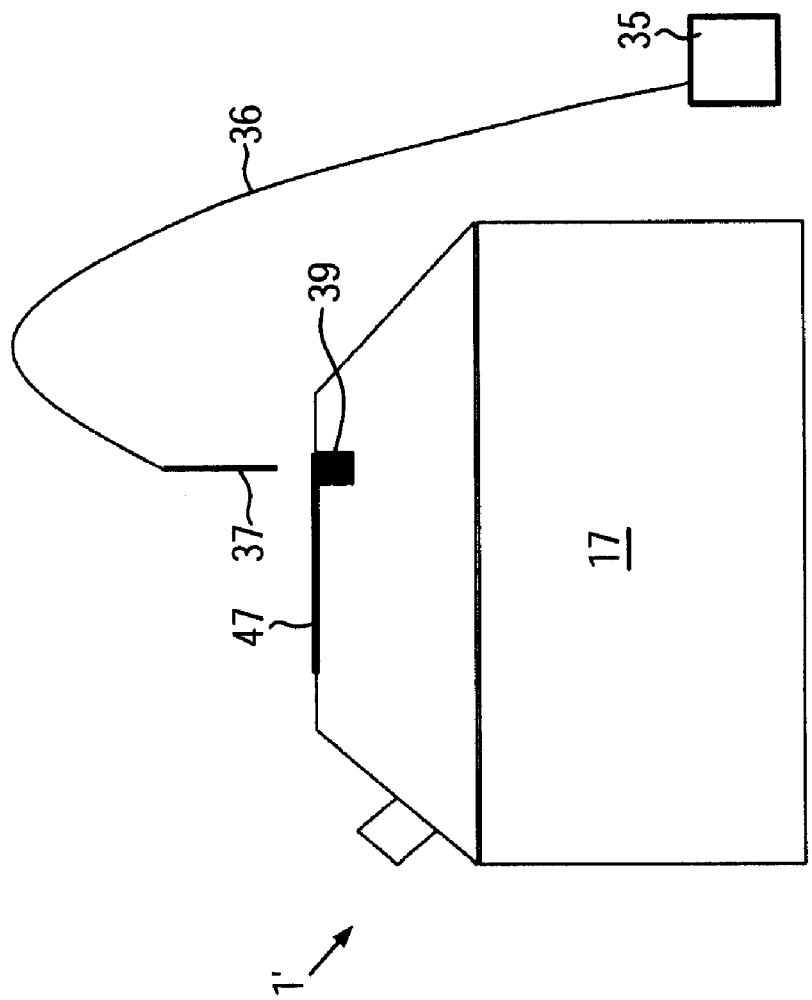
FIG. 5b shows a schematic view of the closable chamber depicted in FIG. 5a, at the closed position.
Figure 5A:
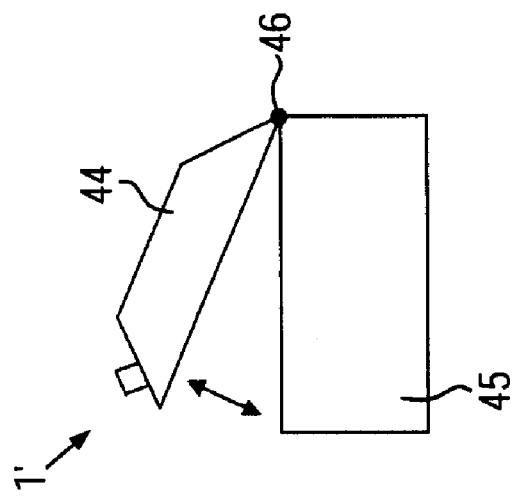
FIG. 5a shows a schematic view of the closable chamber of a chamber machine, at the open position.

FIG. 5a, 5b show in a schematic view a different type of a packaging machine 1' according to the present invention, viz. a so-called chamber machine. In this chamber machine 1', a chamber bottom 45 and a chamber top 44 are provided, which are able to unite, thus forming a chamber 17 around the package 21. The chamber top 44 can be pivoted about a hinge 46 relative to the chamber bottom 45 so as to open the chamber 17. In FIG. 5a, the chamber top 44 is shown in its open position.

FIG. 5b shows the chamber 17 in its closed position. The chamber top 44 has a viewing window 47 provided therein. On the inner side of the chamber top 44, an indicator 39 is attached to the viewing window 47. A measuring head 37 of the measuring device 35 is located outside the chamber top 44, at least, however, outside the interior of the chamber 17. This measuring head 37 is used for reading the indicator 39 by means of electromagnetic radiation to which the viewing window 47 is transparent.

Taking as a basis the embodiments shown, the packaging machines 1 according to the present disclosure can be varied in many different ways. It has already been indicated that the packaging machine 1 may be a deep drawing machine, a chamber machine or a tray sealer. Either one measuring head 37 or a plurality of measuring heads 37 can be provided on the packaging machine 1. Each measuring head 37 can be associated with a separate measuring device 35, or one measuring device can be provided for all the existing measuring heads 37 in common. The reading of the indicator 39 need not take place in the visible part of the electromagnetic spectrum, but such reading may also take place in other spectral regions, e.g. with UV radiation, infrared radiation, terahertz radiation, microwave radiation or radio waves. It is also imaginable that the indicator 39 comprises a plurality of fields, zones or areas, which each indicate the concentration of a specific gas or gas mixture. To this end, the material on each of these fields or areas may be selected in a suitable manner for a particularly strong interaction with the gas in question.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

What is claimed is:

1. A packaging machine for producing closed packages, the packaging machine comprising:
    a sealing station including a chamber that is sealable in an airtight manner around one or more packages;
    a gas flushing unit for flushing with a gas the one or more packages contained in the chamber;
    at least one gas line leading into the chamber or out of the chamber;
    a measuring device for determining a concentration of the gas, the measuring device comprising a measuring head arranged at the sealing station for reading, by means of electromagnetic radiation, an indicator to determine the concentration of the gas, the indicator being arranged in the interior of the chamber, in an interior of a package and/or in an interior of the at least one gas line; and
    a control unit in communication with the measuring device, the control unit being configured to control the gas flushing of the one or more packages based on data obtained by the measuring device.

2. A packaging machine according to claim 1 wherein the measuring head is configured for optically reading the indicator.

3. A packaging machine according to claim 1 wherein the measuring head is arranged in a wall of the chamber or of the at least one gas line.

4. A packaging machine according to claim 1 wherein the measuring head is arranged outside the chamber or the at least one gas line.

5. A packaging machine according to claim 1 wherein the measuring device is configured to optically activate the indicator.

6. A packaging machine according to one to claim 1 wherein the measuring head is configured to measure the reflectivity, the transmissivity and/or the fluorescence of the indicator in a specific spectral region or at a specific wavelength.

7. A packaging machine according to claim 6 further comprising a unit for varying the spectral region or the wavelength.

8. A packaging machine according to claim 1 further comprising a device disposed proximate the indicator for cleaning the indicator.

9. A packaging machine according to claim 8 wherein the control unit is in communication with the cleaning device for automatically operating the cleaning device.

10. A packaging machine according to claim 1 wherein the measuring device is configured to determine respective concentrations of two or more different gases or gas mixtures.

11. A packaging machine according to claim 1 wherein the indicator comprises two or more areas, each of said areas being suitable for indicating concentration of a specific gas or gas mixture.

12. A packaging machine according to claim 1 wherein the measuring device is configured for spectroscopically reading the indicator.

13. A packaging machine according to claim 1 further comprising a device for providing the indicator in the interior of the package.

14. A packaging machine according to claim 13 wherein the providing device is configured to attach the indicator to a side of a cover sheet facing a container part of the package.

15. A packaging machine according to claim 13 wherein the providing device is configured to form the indicator on a side of a cover sheet of the package that faces a container part of the package.

16. A packaging machine according to claim 15 wherein the providing device comprises a printing device.

17. The packaging machine of claim 1 wherein the measuring head emits electromagnetic radiation for interacting with the indicator.

18. The packaging machine of claim 1 wherein the chamber comprises a window that is transparent to the electromagnetic radiation, and the window is arranged between the measuring head and the interior of the chamber.

19. The packaging machine of claim 1 wherein the measuring head is arranged at the chamber.

20. A packaging machine for producing closed packages, the packaging machine comprising:
a chamber that is sealable in an airtight manner around one or more packages;
a gas flushing unit for flushing with a gas the one or more packages contained in the chamber;
at least one gas line leading into the chamber or out of the chamber;
an indicator arranged in an interior of the chamber and/or in an interior of the at least one gas line;
a measuring device comprising a measuring head for reading, by means of electromagnetic radiation, the indicator to determine the concentration of the gas; and
a device disposed proximate the indicator for cleaning the indicator.

21. The packaging machine of claim 20 further comprising an additional measuring device for reading, by means of electromagnetic radiation, an additional indicator disposed in one of the one or more packages.

22. A packaging machine for producing closed packages, the packaging machine comprising:
a chamber that is sealable around one or more packages;
a gas flushing unit for flushing with a gas the one or more packages received in the chamber;
a gas line in communication with the chamber; and
a measuring device comprising a measuring head that is configured to emit electromagnetic radiation and to read, through the use of the electromagnetic radiation, an indicator to determine the concentration of the gas, the indicator being arranged in an interior of the chamber, in an interior of one of the one or more packages, or in an interior of the gas line;
wherein the chamber comprises a sealing tool having a window, and the window is disposed between the measuring head and the interior of the chamber such that the electromagnetic radiation may pass through the window.

23. A packaging machine for producing closed packages, the packaging machine comprising:
a chamber that is sealable around one or more packages;
a gas flushing unit for flushing with a gas the one or more packages received in the chamber;
a gas line in communication with the chamber;
an indicator arranged in an interior of the gas line; and
a measuring device comprising a measuring head that is configured to emit electromagnetic radiation and to read, through the use of the electromagnetic radiation, the indicator to determine the concentration of the gas;
wherein the chamber comprises a sealing tool having a wall and a window, the measuring head is disposed in the wall of the sealing tool, and the window is disposed between the measuring head and the interior of the gas line such that the electromagnetic radiation may pass through the window.

* * * * *

UNITED STATES PATENT AND TRADEMARK OFFICE
CERTIFICATE OF CORRECTION

PATENT NO. : 8,397,475 B2
APPLICATION NO. : 12/786748
DATED : March 19, 2013
INVENTOR(S) : Hans-Joachim Boekstegers et al.

It is certified that error appears in the above-identified patent and that said Letters Patent is hereby corrected as shown below:

In the Claims:

Column 8, Line 47, Claim 6:

After "A packaging machine according" delete "to one"

Signed and Sealed this
Twenty-third Day of July, 2013

Teresa Stanek Rea
*Acting Director of the United States Patent and Trademark Office*